United States Patent [19]

Lyons et al.

[11] Patent Number: 5,345,008
[45] Date of Patent: Sep. 6, 1994

[54] DECOMPOSITION OF ORGANIC HYDROPEROXIDES WITH NITRATED PORPHYRIN COMPLEXES

[75] Inventors: James E. Lyons, Wallingford; Paul E. Ellis, Jr., Downingtown, both of Pa.

[73] Assignee: Sun Company, Inc. (R&M), Philadelphia, Pa.

[21] Appl. No.: 73,840

[22] Filed: Jun. 9, 1993

[51] Int. Cl.$^5$ ............ C07C 29/48; C07C 31/00; C07C 33/00
[52] U.S. Cl. .................. 568/909.8; 568/815
[58] Field of Search ............ 568/815, 909.8

[56] References Cited

U.S. PATENT DOCUMENTS

| | | | |
|---|---|---|---|
| 3,401,193 | 9/1968 | Farrissey | 260/488 |
| 3,864,216 | 2/1975 | Worrell et al. | 203/49 |
| 3,879,467 | 4/1975 | Zajacek et al. | 260/586 P |
| 3,925,316 | 12/1975 | Brunie et al. | 260/586 R |
| 4,022,034 | 5/1977 | Matsuda | 66/169 R |
| 4,173,587 | 11/1979 | Wu et al. | 260/593 A |
| 4,257,852 | 3/1981 | Worrell | 203/99 |
| 4,296,262 | 10/1981 | Grane et al. | 568/910 |
| 4,551,553 | 11/1985 | Taylor et al. | 568/311 |
| 4,803,187 | 2/1989 | Lyons et al. | 502/200 |
| 4,859,798 | 8/1989 | Lyons et al. | 568/399 |
| 4,895,680 | 1/1990 | Ellis, Jr. et al. | 260/410.9 R |
| 4,895,682 | 1/1990 | Ellis, Jr. et al. | 260/410.9 R |
| 4,898,989 | 2/1990 | Ellis, Jr. et al. | 568/399 |
| 4,900,871 | 2/1990 | Ellis, Jr. et al. | 568/399 |
| 4,910,349 | 3/1990 | Sanderson et al. | 568/909.8 |
| 4,912,266 | 3/1990 | Sanderseon et al. | 568/909.8 |
| 4,912,267 | 3/1990 | Sanderson et al | 568/909.8 |
| 4,916,101 | 4/1990 | Lyons et al. | 502/209 |
| 4,922,033 | 5/1990 | Sanderson et al. | 568/909.8 |
| 4,922,034 | 5/1990 | Sanderson et al | 568/909.8 |
| 4,922,036 | 5/1990 | Sanderson et al. | 568/909.8 |
| 4,922,035 | 5/1990 | Sanderson et al. | 568/909.8 |
| 4,970,348 | 11/1990 | Ellis, Jr. et al. | 568/399 |
| 4,978,799 | 12/1990 | Sanderson et al. | 568/385 |
| 4,992,602 | 2/1991 | Sanderson et al. | 568/909.8 |
| 5,004,837 | 4/1991 | Bauer et al. | 568/342 |

FOREIGN PATENT DOCUMENTS

0308101  3/1989  European Pat. Off. .

OTHER PUBLICATIONS

V. M. Nekipelov, "Use of the Proton NMR Relaxation Method to Study the Coordination of Cumene Hydroperoxide with Cobalt and Ruthenium Carboxylates", Dokl. Akad, Nauk SSSR, V 261 (6), 1377–1381 (1981).

A. M. Trzeciak et al, "NMR Studies of Mu3–Oxotriruthenium Hexacarboxylate Cumene Hydroperoxide Interaction", Oxid. Commun., V. 1(4), pp. 295–303 (1980).

A. M. Trzeciak et al, "Cumene Hydroperoxide Decomposition Reaction Catalyzed by Ruthenium (III) beta-diketonates", React. Kinet. Lett., V. 12(1–2), pp. 121–125 (1981).

Yu. A. Aleksandrov, Ah. Obshsch. Khim., "Decomposition of Organic Hydroperoxides on Ruthenium-pi.-Complexes", V.48, p. 2141 (1978).

J. E. Lyons & P. E. Ellis, Jr., "Selective Low Temperature Hydroxylation of Isobutane by Molecular Oxygen Catalyzed by an Iron Perhaloporphyrin Complex", Catalysis Letters, 8, 45 (1991).

R. J. Donohoe et al, "Characterization of Singly Reduced Iron (II) Porphyrins", J. Amer. Chem. Soc., 109, 5593 (1987).

L. C. Gong et al, "Nirtooctaethylporphyrins: synthesis, optical and redox properties", Can. J. Chem., 63, 401–5 (1985).

Catalano et al, "Control of Reactivity at the Porphyrin Periphery by Metal Ion Co–ordination", J. Chem. Soc., 1535 (1984).

*Primary Examiner*—Werren B. Lone
*Attorney, Agent, or Firm*—Q. Todd Dickinson; Stephen T. Falk

[57] ABSTRACT

Hydroperoxides are decomposed by contact with metalloporphyrin coordination complex catalysts in which hydrogen in the porphyrin molecule has been substituted with at least one nitro group and may be further substituted with other electron-withdrawing elements or groups, for example, halogen or halocarbons, or with hydrocarbon groups. Preferred catalysts are iron tetranitro-$\beta$-octaethylporphyrins and iron tetrakispentafluorophenyl-$\beta$-nitroporphyrins.

34 Claims, No Drawings

DECOMPOSITION OF ORGANIC HYDROPEROXIDES WITH NITRATED PORPHYRIN COMPLEXES

This invention relates to the decomposition of organic hydroperoxides with metal catalysts which provide desirably high reaction rates, to produce the corresponding alcohol. The catalysts employed according to the invention provide very high reaction rates at relatively low temperatures such as room temperature, in contrast to prior art catalysts which catalyze decomposition of organic hydroperoxides much more slowly and require elevated temperatures in order to achieve satisfactory reaction rates.

BACKGROUND OF THE ART

Sanderson et al., U.S. Pat. No. 4,910,349, disclose the preparation of t-butyl alcohol by the catalytic decomposition of t-butyl hydroperoxide (TBHP), preferably in solution in t-butyl alcohol, in the presence of a metal phthalocyanine of a metal of Group IB, Group VIIB or Group VIIIB, for example chloroferric phthalocyanine and rhenium heptoxide-p-dioxane or oxotrichloro-bis-(triphenylphosphine) rhenium V. Various ratios of Fe to Re and Fe +Re to TBHP were studied.

Sanderson et al., U.S. Pat. No. 4,922,034, disclose decomposition of t-butyl hydroperoxide to t-butyl alcohol using a metal porphine catalyst, for example tetraphenylporphine, optionally promoted with a thiol and a heterocyclic amine.

Sanderson et al., U.S. Pat. No. 4,912,266, disclose decomposition of t-butyl hydroperoxide with an imidazole-promoted metal PCY catalyst, for example Fe(III)-PCYCl or Mn (II) PCY or VOPCY.

Marquis et al., U.S. Pat. No. 4,992,602, disclose a continuous method for converting isobutane to isobutyl alcohol including the step of decomposing t-butyl hydroperoxide to t-butyl alcohol, using a monocyclic aromatic solvent and a PCY decomposition catalyst.

Derwent abstract (Week 8912, Other Aliphatics, page 58) of reference 89-087492/12 (EP 308-101-A) discloses decomposition of t-butyl hydroperoxide to t-butyl alcohol using a metal porphine catalyst such as a trivalent Mn or Fe tetraphenylporphine, optionally promoted with an amine or thiol, or a soluble Ru catalyst promoted with a bidentate ligand such as Ru(acac)3 promoted with bis(salicylidene)-ethylenediamine, or a promoted PCY catalyst such as a Mn, Fe or vanadyl PCY promoted with an amine, a Re compound such as NH4ReO4, a mercaptan and a free radical inhibitor, a base or a metal borate.

Lyons et al., U.S. Pat. No. 5,120,886, issued Jun. 9, 1992, which is incorporated by reference herein, teaches decomposition of hydroperoxides with metal ligand complexes in which hydrogen in the ligand molecule has been substituted with electron-withdrawing elements or groups, for example halogen or nitro or cyano groups.

Related catalysts to those used according to the invention have been previously disclosed for use in oxidizing alkanes to the corresponding alcohols. For example, perhalogenated metal complexes have been disclosed in Ellis et al., copending application Ser. No. 07/568,116, filed Aug. 16, 1990, the disclosure of which is herein incorporated by reference. Other patents disclosing use of metal coordination complex catalysts in oxidation of alkanes are Ellis et al U.S. Pat. Nos. 4,895,680; 4,895,682 and 4,970,348.

BACKGROUND OF THE INVENTION

The decomposition of hydroperoxides to give the corresponding alcohol has potential commercial importance. Alkyl hydroperoxides are products of alkane oxidation and their alcohol decomposition products are useful fuel and chemical products. Specifically, t-butyl hydroperoxide is made by the oxidation of isobutane and can be decomposed to the high octane fuel additive, t-butyl alcohol, in the presence of metal complexes. Elevated temperature and/or high catalyst concentration is often needed, and product selectivity is often below 90%.

The present invention provides a process for decomposing hydroperoxides to the corresponding alcohol which gives a desired decomposition at a faster rate, allowing lower temperatures and/or lower catalyst concentrations than those required in the prior art and a higher product selectivity at a given reaction temperature. The greater activity of the catalysts of this invention allows them to be used in much lower concentrations, resulting in considerable savings in catalyst costs. The process of the invention provides the above and/or other advantages in the decomposition of organic hydroperoxides generally to the corresponding alcohols.

SUMMARY OF THE INVENTION

The catalyst useful in the present invention is a metalloporphyrin coordination complex catalyst containing a transition metal center, having the structure:

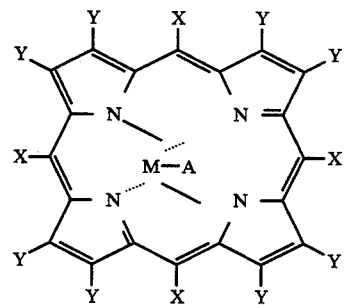

where M is Fe, Mn, Co, Cu, Ru or Cr, Fe being preferred; X is one or more electron-withdrawing substituents for meso-hydrogen atoms in the porphyrin molecule which are selected from the group consisting of nitro, halogen, hydrocarbon and halocarbon or combinations thereof; Y is one or more electron-withdrawing substituents for $\beta$-hydrogen atoms in the porphyrin molecule which are selected from the group consisting of nitro, halogen, hydrocarbon and halocarbon or combinations thereof; at least one of X or Y is nitro; A is anion or is absent. Preferred anions are azide, halide, hydroxide or nitride. The catalysts include complexes of $\mu$ oxo dimers comprising two structures as shown above joined through a M—O—M linkage.

DETAILED DESCRIPTION OF THE INVENTION

The present invention comprises a process for the decomposition of hydroperoxides. The process, utilizing the catalysts described below, is carried out in any conventional manner known in the art. The decomposition is preferably performed with the hydroperoxide in a suitable organic solvent. A useful solvent is the alcohol which is formed by the decomposition of the hydroperoxide. Any suitable temperature and pressure may be used; such parameters are well known to those skilled in the art. A preferred temperature is in the range of 25° to 125° C. In view of the reaction rate of the catalysts used in the invention, the reaction times are fairly short; in the range of 0.1 to 5 hours, preferably 0.1 to 1 hour.

The catalyst useful in the present invention is a metalloporphyrin coordination complex catalyst containing a transition metal center having the structure:

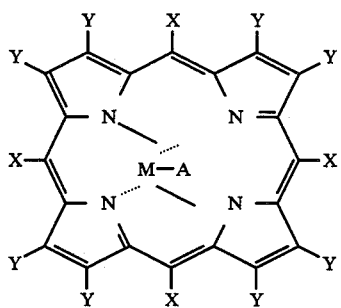

where M is Fe, Mn, Co, Cu, Ru or Cr, Fe being preferred; X is one or more electron-withdrawing substituents for meso-hydrogen atoms in the porphyrin molecule which are selected from the group consisting of nitro, halogen, hydrocarbon and halocarbon or combinations thereof; Y is one or more electron-withdrawing substituents for $\beta$-hydrogen atoms in the porphyrin molecule which are selected from the group consisting of nitro, halogen, hydrocarbon and halocarbon or combinations thereof; at least one of X or Y is nitro; A is anion or is absent. Preferred anions are azide, halide, hydroxide or nitride. The catalysts include complexes of $\mu$-oxo dimers comprising two structures as shown above joined through a M—O—M linkage.

From the foregoing it will be seen that the catalysts used in the process of the invention are comprised of the component parts: the ligand moiety, which has been substituted with electron-withdrawing elements or groups, for example having been substituted with nitro groups or having been halogenated, the metal center which is bound to (i.e., complexed with) the ligand, and as anion, azide, chloride, hydroxide or nitride or the like, which is bound to the metal. The metal-ligand portion is also frequently described in the art as a metal coordination complex.

A preferred embodiment of the catalyst found useful in the present invention is a metalloporphyrin coordination complex catalyst containing a transition metal center and a halogenated ligand, where the ligand is for example tetraphenylporphyrin, related porphyrinato ligands, porphycenes, porphenes, and related macrocules phthalocyanines, 1,3-bis(2-pyridylimino) isoindoline ("BPI") and other 1,3-bis(arylimino) isoindolines. Preferably the transition metal is iron and the ligand is a porphyrin.

The term "ligand" is used herein in its conventional meaning and refers generically to a group or system of atoms which form one or more bonds to a metal ion, i.e., forms a coordination complex, and stabilizes the coordination complex in desirable oxidation states. Suitable ligands for the present purpose are the well-known porphyrins such as alkyl and aryl porphyrins such as octaethylporphyrins (OEP), tetraphenylporphyrins (TPP), tetramethylporphyrins and the like. Usually there are 0–12 substituents, alkyl or aryl, on the basic porphyrin structure, the alkyls are $C_1$–$C_4$ and the aryls contain 1 or 2 rings which may themselves have alkyl substituents. The ligand itself may be halogenated by replacement of hydrogen atoms therein with halogen atoms (i.e. fluorine, chlorine or bromine or a combination thereof). Halogenation, and particularly perhalogenation in which all or substantially all of the hydrogen has been replaced by halogens, has been found to increase the activity of these catalysts for the decomposition of hydroperoxides by increasing the rate of decomposition to the desired products. The preferred halogen is fluorine.

The preferred ligands are those in which nitro groups have been substituted for hydrogen in the ligand molecule. These nitro-substituted ligands may additionally contain halogen substituted for hydrogen in the ligand molecule. These substituents are believed to act as electron-withdrawing agents when the ligand is used as a catalyst for the decomposition of hydroperoxides.

Other electron-withdrawing substituents than nitro or halogen may also be substituted at the meso or $\beta$-position of the ligand, such as hydrocarbon or halocarbon groups. Suitable hydrocarbon groups include $C_1$–$C_4$ alkyls or aryls containing 1 or 2 rings which may themselves have alkyl substituents. Preferred hydrocarbon groups are ethyl and phenyl groups. Such alkyl and aryl substituents may themselves be halogenated. Preferred halocarbon groups include halomethyl and halophenyl groups, e.g. trifluoromethyl, pentafluorophenyl.

The catalyst according to this embodiment of the invention may have, in addition to the halogen atoms in the ligand, an anion, A, which may comprise any conventional salt, including but not limited to chloride, fluoride, bromide, iodide, azide, hydroxide or nitride.

The use of nitrated metalloporphyrins as catalysts for the decomposition of hydroperoxides is one particularly preferred embodiment of the invention. An examples of making such catalysts in the art includes successive nitration at the meso-positions of Zn(octaethylporphine), eventually yielding Zn(meso-tetranitrooctaethyl porphine). L. C. Gong and D. Dolphin, Can. J. Chem, 63,401–5(1985). Other workers such as Catalano et al in J. Chem. Soc., 1535 (1984) have been able to nitrate the beta or pyrrolic positions in various metal tetraphenylporphyrins. According to one embodiment of the present invention, meso-nitrated metalloporphyrins are used in catalytic decomposition of hydroperoxides. A preferred embodiment comprises an iron meso-tetranitro-octaethylporphyrin as the decomposition catalyst.

The use of $\beta$-substituted meso-nitrated metalloporphyrin catalysts in the present process comprises one embodiment of the invention. Two or more meso-nitro group substituent are preferred; four being more preferred. The $\beta$ (i.e., pyrrolic) positions on the porphyrin macrocycle are substituted by electron-withdrawing groups, such as halogen, hydrocarbon and halocarbon groups. Among the halogens, fluoride, chloride and bromide are preferred. Suitable hydrocarbon groups include $C_1$–$C_4$ alkyls or aryls containing 1 or 2 rings which may themselves have alkyl substituents. Preferred hydrocarbon groups are ethyl and phenyl groups. Such alkyl and aryl substituents may be halogenated. A particularly preferred embodiment comprises an iron (tetranitro-octaethylporphyrin).

Another embodiment of the present invention employs meso-nitrated porphyrins further nitrated at the β-position of the macrocycle. Non-nitrated meso and βpositions may be halogenated. When nitro groups are substituted in β-positions, care should be exercised to avoid creation of explosive compositions or to handle such compositions with caution.

The use of meso-substituted β-nitrated metalloporphyrin catalysts in the present process comprises a further embodiment of the invention. The substituents for hydrogen in the meso positions on the porphyrin macrocycle comprise halogen, hydrocarbon and halocarbon. Among the halogens, fluoride, chloride and bromide are preferred. Suitable hydrocarbon groups include $C_1$-$C_4$ alkyls or aryls containing 1 or 2 rings which may themselves have alkyl substituents. Preferred hydrocarbon groups are ethyl and phenyl groups. Suitable halocarbon groups include halogenated $C_1$-$C_4$ alkyls or aryls containing 1 or 2 rings which may themselves have alkyl substituents. Preferred halocarbon groups are pentafluorphenyl, pentachlorophenyl, trifluoromethyl and trichloromethyl groups. A particularly preferred embodiment comprises tetrakispentafluorophenyl β-nitroporphyrin with up to eight β-nitro groups. Non-nitrated β-positions may be halogenated.

In the meso-substituted β-nitrated catalysts, the meso position electron-withdrawing component of the ligand, X, can be nitro, halogen, hydrocarbon or halocarbon or combinations thereof. Two or more meso-nitro group substituents are preferred; four being more preferred. Suitable halogens are fluoride, chloride, bromide, iodide or combinations thereof. Preferably among the halogens is one of the first three mentioned, more preferably fluoride. We have found that complete halogenation, or perhalogenation, may provide substantially superior results.

The non-nitrated β-positions in the meso-substituted β-nitro porphyrin, Y, can be halogen, hydrocarbon or halocarbon or mixtures thereof. Preferable among the halogens are fluoride, chloride and bromide, more preferably fluoride. The degree of ligand halogenation should be substantially complete, i.e., perhalogenation. If none of X are nitro, then at least one Y substituent must be nitro.

One method of preparing the catalysts of the present invention is by modifying procedures described in the art for preparing unhalogenated ligands. For example, the unhalogenated Fe(TPP) Cl complex (in which "TPP" is tetraphenylporphyrinato) can be prepared by a standard method in which (TPP)H$_2$ and Fe(II) (or other metal) chloride are refluxed together in a dimethylformamide solution. (See, e.g., A. D. Adler et al, *J. Inorg. Nucl. Chem.*, 32, 2443 (1970).) From these metal salts the corresponding azides may be prepared by metathesis reactions with dissolved NaN$_3$ or hydrazoic acid. The preparation techniques of Lyons et al., U.S. Pat. No. 5,120,886, are incorporated herein by reference.

By way of specific illustration, the tetra-meso-nitrated metal porphyrin, [Fe(NO$_2$)$_4$(OEP)]Cl, iron tetranitro-octaethylporphyrin, may be prepared as follows: 10-15 equivalents of NO$_2$ are reacted with Fe (OEP) Cl in CH$_2$Cl$_2$ in the presence of an anion exchange resin. Fe (OEP) Cl may be prepared by standard techniques known in the art. (See, e.g., D. O. Cheng and E. P. LeGoff, *Tett. Lett.*, 1469 (1977).) The reaction is performed at room temperature and is run for one hour.

An example of a suitable anion exchange resin is Rohm & Haas Co.'s Amberlite ® IRA-904. After chromatography on alumina, the complex [Fe(NO$_2$)$_4$(OEP)]$_2$O is obtained. In this compound the four meso positions on the porphyrin ligand are nitrated.

One method for the preparation of the chloride salt [Fe(NO$_2$)$_4$(OEP)]Cl involves reacting the μ-oxo dimer with 6N HCL for approximately 2 minutes with shaking. The azide salt [Fe(NO$_2$)$_4$(OEP)]N$_3$ can be produced by reacting the chloride salt with a tenfold excess of NaN$_3$ in acetone.

A catalyst used in the process according to the invention may also be prepared by the method disclosed and claimed in Ellis et al U. S. Pat. application Ser. No. 07/634,261 filed Dec. 7, 1990, the disclosure of which is herein incorporated by reference. As a typical reaction according to that application, the perhalogenation is performed by reaction of iron (tetrakispentafluorophenyl) porphyrinato with bromine.

In some cases, dimetal μ-oxo compounds, commonly known as μ-oxo dimers, are also suitable catalysts for the present process. In these compounds, each of the two iron centers is bound to one anion moiety. The linkage can be shown as M—O—M which depicts the metal centers of two coordination complexes bound to a common oxygen atom. A typical structure for such compounds is:

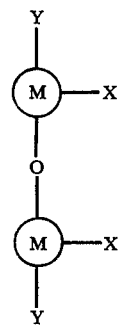

where ◯ is the ligand and M, X and Y are as previously defined. This compound may also be characterized by the structure:

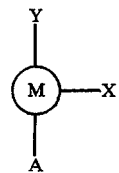

where ◯, M, X and Y are as previously defined and A is:

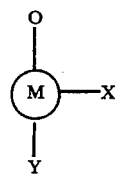

β-Nitro-substituted porphyrins are prepared, for example, by reacting iron tetrakispentafluorophenyl chloride with 1 to 8 or excess equivalents of nitrogen dioxide in methylene chloride or other solvents known in the nitration arts, such as chloroform and methyl isobutyl ketone, leading to various amounts of nitration at the beta positions on the ring according to the severity of the reaction conditions. Beta positions left unnitrated are subsequently halogenated using conventional chlorination, bromination or fluorination techniques. The general structure for this preparation is:

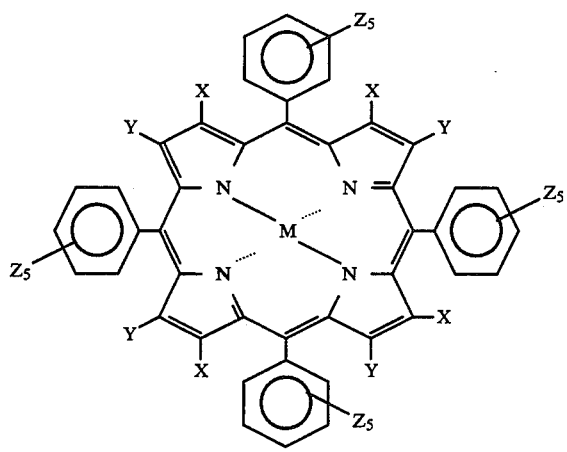

where M is Fe, Cr, Mn, Ru, Co, or Cu; X is NO₂; Y is NO₂, Cl Br or F; and Z is, Cl or F. Fe(porphine)Cl is reacted with an excess of nitrogen dioxide in methylene chloride to produce Fe(mesotetranitroporphine). The μ-oxo, chloride and azido salts are then prepared according to the conventional methods known in the art. The beta or pyrrolic hydrogens can be further nitrated or halogenated as desired. The general structure for this preparation is:

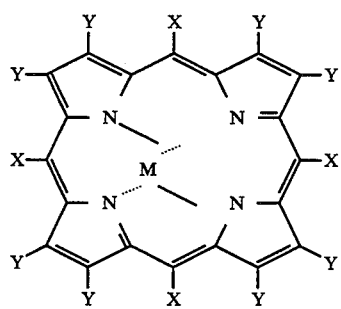

where M is Fe, Cr, Mn, Ru, Cu or Co; X is NO₂; Y is NO₂, Cl, F, Br or any combination thereof. Meso-perfluorinated alkyl porphyrins as disclosed in copending application Ser. No. 568,116, filed Aug. 16, 1990, the disclosure of which is incorporated by reference herein, can be nitrated in the β(i.e. pyrrolic) positions using nitrogen dioxide in methylene chloride or nitric/sulfuric acid nitrating solutions. The general structure for this preparation is:

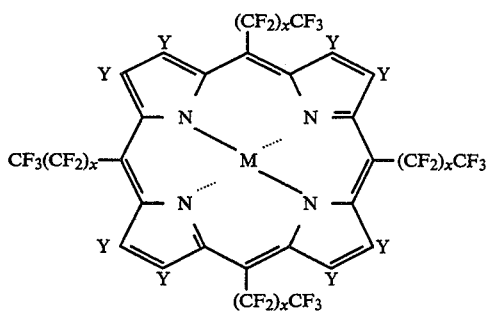

where M is Fe, Cr, Mn, Ru, Cu or Co; X is 0 to 6; and Y is NO₂ and Cl, Br or F.

The decomposition of hydroperoxide according to the invention is preferably carried out in a solution of the hydroperoxide, preferably a solution containing from about 5 to about 50 wt. % of hydroperoxide. Suitable solvents include benzene, chlorobenzene, o-dichlorobenzene, acetonitrile, benzonitrile, alcohols, ketones and the like. A useful solvent is the alcohol which corresponds to that formed by decomposition of the hydroperoxide, for example, t-butanol formed by decomposition of t-butyl hydroperoxide.

Any suitable temperature and pressure may be used. Preferably the temperature is in the range from 0° to 200° C., more preferably 25° to 125° C. The pressure may be adjusted as necessary to accomplish decomposition; preferably 15 to 1000 psig, more preferably 15 to 100 psig. The time of reaction may be relatively short, in view of the rapid reaction rate with the catalysts employed according to the invention, but will typically be in the range from 0.1 to 5 hours, preferably 0.1 to 1 hour.

In the process of the invention, the hydroperoxide dissolved in a solvent is introduced into a reaction zone wherein it is contacted with catalyst, in the substantial absence of additional oxidizing agent, to convert the hydroperoxide, ROOH, where R is an organic radical, to the corresponding alcohol, ROH.

Hydroperoxides which may be decomposed according to the invention include compounds having the formula ROOH, where R is an organic radical, typically a straight or branched chain alkyl or cycloalkyl group containing 2 to 15 carbon atoms, an aryl group such as a monocyclic or polycyclic group in which the cyclic groups may optionally be substituted with one or more substituents inert to the decomposition reaction, such as alkyl or alkoxy, containing 1 to 7 carbon atoms, nitro, carboxyl or carboxyl ester containing up to about 15 carbon atoms and a halogen atom such as chloride, bromide, or an alkaryl group in which the alkyl chain contains from 1 to 15 carbon atoms and the aryl group is as above described. Preferably, R is an alkyl or cycloalkyl group containing 4 to 12 carbon atoms or an alkaryl group in which the aromatic moiety is phenyl and the alkyl substituent is straight or branched chain alkyl or cycloalkyl containing up to about 6 carbon atoms. Examples are t-butyl and isobutyl hydroperoxide, iso-amyl hydroperoxide, 2-methylbutyl-2-hydroperoxide, cyclohexyl hydroperoxide, cumyl hydroperoxide, phenethyl hydroperoxide and cyclohexylphenyl hydroperoxide. Phenethyl hydroperoxide and cumyl hydroperoxide are converted to phenethyl alcohol and cumyl alcohol, respectively.

The following examples illustrate the invention:

EXAMPLE 1

Catalyst was stirred into a mixture of 23 ml tertiary butyl alcohol (TBA) and 15.3 ml tertiary butyl hydroperoxide (tBHP). The concentration of catalyst is indicated in Table I. Oxygen gas was measured manometrically as it evolved. The catalyst was an iron porphyrin complex as shown in Table I. The results are shown for halogenated and unhalogenated non-nitrated iron alkylporphyrin complexes and for tetranitro μ-oxo dimer complexes.

EXAMPLE 2

Catalyst was stirred into 6–7 ml isobutane in 30 ml benzene. The mixture was heated and stirred at the reaction temperature (as stated in Table II) and the pressure was raised to 100 psig with $O_2$. Alkane oxidation was gauged by measuring the production of tertiary butyl alcohol (TBA). The concentration of iron complex catalyst is indicated in Table II as a measure of iron concentration (mmole Fe). The results of four different complexes are shown in Table II.

TABLE I

Decomposition of t-Butyl Hydroperoxide Catalyzed by Iron Metalloporphyrin Complexes

| Catalyst | Conc. ppm | Reaction Time, hrs | $O_2$ Evolved cc | tBHP Conv. % |
|---|---|---|---|---|
| Fe(OEP)Cl | 22 | 1 | 205 | <15 |
| Fe(TPP)Cl | 25 | 1 | 345 | NA |
| [Fe(TPPF$_{20}$)]$_2$O | 28 | 1 | 840 | |
| | | 4.25 | 1307 | >95 |
| [Fe(TN)(OEP)]$_2$O | 28 | 1 | 1335 | 99 |
| [Fe(TN)(OEP)]$_2$O | 16 | 0.8 | 1260 | >90 |
| | | 1 | 1260 | >90 |
| [Fe(TN)(OEP)]$_2$O | 10 | 1 | 955 | |
| | | 3 | 980 | NA |
| Fe(TPPF$_{20}$Cl$_8$)Cl | 12 | 1 | 1230 | |
| | | 2 | 1330 | >95 |

TN = meso tetranitro
OEP = β-octaethylporphyrin
TPP = meso tetraphenylporphyrin

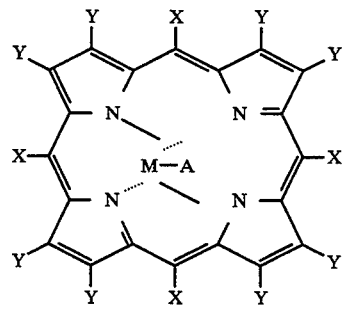

wherein M is selected from the group consisting of Fe, Mn, Co, Cu, Ru and Cr; at least one X is nitro and the remaining X are selected from the group consisting of hydrogen, nitro fluorine, chlorine, bromine, hydrocarbon and halocarbon or combinations thereof; Y is selected from the group consisting of hydrocarbon, halocarbon, fluorine, chlorine, bromine and hydrogen or combinations thereof; and A is anion or is absent.

2. The process of claim 1 wherein all X comprise nitro and all Y comprise hydrocarbon.

3. The process of claim 2 wherein said hydrocarbon is selected from the group consisting of alkyl and aryl groups.

4. The process of claim 3 wherein said hydrocarbon comprises ethyl.

5. The process of claim 1 wherein M comprise iron.

6. The process of claim 1 wherein A is selected from the group consisting of halide, hydroxide, azide and nitride.

7. The process of claim 6 wherein A comprises chloride.

8. The process of claim 7 wherein said catalyst comprises iron(tetranitro-octaethylporphyrin) chloride.

9. The process of claim 1 wherein said catalyst comprises μ-oxo dimer comprising two complexes as shown in claim 1 joined through a M—O—M linkage.

TABLE II

Oxidation of Isobutane Catalyzed by Iron Metalloporphyrin Complexes

| Catalyst | Conc. mmole Fe | Turnover T = 60° C. | Select. | Turnover T = 80° C. | Select. |
|---|---|---|---|---|---|
| Fe(OEP)Cl | 0.013 | 0 | — | 0 | — |
| [Fe(TPP)]$_2$O | 0.013 | 0 | — | 0 | — |
| [Fe(TPPF$_{20}$)]$_2$O | 0.013 | 1290 | 86 | 2560 | 80 |
| [Fe(TN)(OEP)]$_2$O | 0.013 | 800 | 88 | 1680 | 88 |

Turnover (at Temperature indicated) = moles of (TBA + Acetone)/moles catalyst
Select. = Selectivity = (moles TBA produced/Total moles liquid product) × 100

What is claimed is:

1. A process for the decomposition of organic hydroperoxide which comprises contacting said hydroperoxide with a catalyst comprising:

10. The process of claim 9 wherein said catalyst comprises a μ-oxo dimer of iron(tetranitrooctaethylporphyrin).

11. A process for the decomposition of organic hydroperoxide which comprises contacting said hydroperoxide with a catalyst comprising:

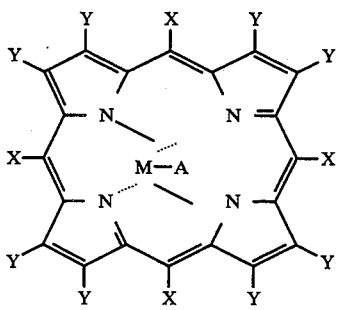

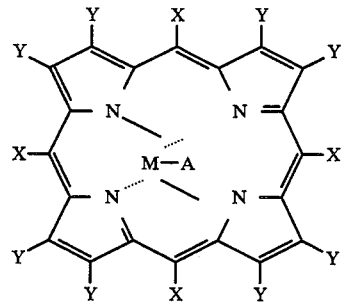

wherein M is selected from the group consisting of Fe, Mn, Co, Cu, Ru and Cr; at least one X is halocarbon and remaining X are selected from the group consisting of hydrogen, halocarbon fluorine, chlorine, bromine and hydrocarbon or combinations thereof; at least one Y is nitro and the remaining Y are selected from the group consisting of nitro, hydrogen, fluorine, chlorine and bromine or combinations thereof; and A is anion or is absent.

12. The process of claim 11 wherein all X comprise halocarbon.

13. The process of claim 12 wherein said halocarbon comprises perhalogenated halocarbon.

14. The process of claim 13 wherein halogen in said perhalogenated halocarbon is selected from the group consisting of fluorine, chlorine and bromine.

15. The process of claim 14 wherein said perhalogenated halocarbon is selected from the group consisting of pentafluorophenyl, pentachlorophenyl, trifluoromethyl and trichlorophenyl groups.

16. The process of claim 15 wherein said perhalogenated halocarbon comprises pentafluorophenyl group.

17. The process of claim 11 wherein M comprises iron.

18. The process of claim 11 wherein A is selected from the group consisting of halide, hydroxide, azide and nitride.

19. The process of claim 18 wherein A comprises chloride.

20. The process of claim 19 wherein said catalyst comprises iron (tetrakispentafluorophenyl-nitroporphyrin) chloride.

21. The process of claim 11 wherein said catalyst comprises $\mu$-oxo dimer comprising two complexes as shown in claim 11 joined through a M—O—M linkage.

22. The process of claim 21 wherein said catalyst comprises a $\mu$-oxo dimer of iron(tetrakispentafluorophenyl-nitroporphyrin).

23. A process for the decomposition of organic hydroperoxide which comprises contacting said hydroperoxide with a catalyst comprising:

wherein M is selected from the group consisting of Fe, Mn, Co, Cu, Ru and Cr; at least one X is nitro and the remaining X are selected from the group consisting of hydrogen, nitro, fluorine, chlorine and bromine or combinations thereof; at least one Y is nitro and the remaining Y are selected from the group consisting of nitro, hydrogen, fluorine, chlorine and bromine or combinations thereof; and A is anion or is absent.

24. The process of claim 23 wherein all X and all Y comprise nitro.

25. The process of claim 23 wherein M comprises iron.

26. The process of claim 23 wherein A is selected from the group consisting of halide, hydroxide, azide and nitride.

27. The process of claim 26 wherein A comprises chloride.

28. The process of claim 23 wherein said catalyst comprises $\mu$-oxo dimer comprising two complexes as shown in claim 22 joined through a M—O—M linkage.

29. The process of Claims 1, 11 or 23 wherein said hydroperoxides comprise R—O—OH , wherein R is selected from the group consisting of alkyl and aryl groups.

30. The process of claim 29 wherein said hydroperoxide is selected from the group consisting of t-butyl hydroperoxide, isobutyl hydroperoxide, isoamyl hydroperoxide, 2-methylbutyl-2-hydroperoxide, cyclohexyl hydroperoxide, cumyl hydroperoxide, phenethyl hydroperoxide and cyclohexyl hydroperoxide.

31. The process of claim 30 wherein said hydroperoxide comprises t-butyl hydroperoxide.

32. The process of claim 1, 11 or 23 wherein said decomposition is performed in a solution comprising 5 to 50 wt.% of said hydroperoxide, at temperature in the range of 0° to 200° C., and pressure in the range of 15 to 1000 psig, for 0.1 to 5 hours.

33. The process of claim 32 wherein said hydroperoxide is maintained in a solution of organic solvent selected from the group consisting of benzene, chlorobenzene, o-dichlorobenzene, acetonitrile, benzonitrile, ketone and alcohol.

34. The process of claim 33 wherein said alcohol comprises an alcohol corresponding to that formed by decomposition of said hydroperoxide.

* * * * *